(12) United States Patent
Mowat et al.

(10) Patent No.: US 6,464,936 B1
(45) Date of Patent: Oct. 15, 2002

(54) IRRADIATION DEVICE AND METHOD FOR FLUIDS ESPECIALLY FOR BODY FLUIDS

(75) Inventors: David McIvor Mowat, Edinburgh; Ian David Cameron, Dundee; Andrew Gunn, Angus, all of (GB)

(73) Assignee: Iatros Limited, Edinburgh (GB)

( * ) Notice: Subject to any disclaimer, the term of this patent is extended or adjusted under 35 U.S.C. 154(b) by 0 days.

(21) Appl. No.: 09/194,931

(22) PCT Filed: Aug. 18, 1997

(86) PCT No.: PCT/DE97/01822

§ 371 (c)(1),
(2), (4) Date: Feb. 4, 1999

(87) PCT Pub. No.: WO97/46271

PCT Pub. Date: Dec. 11, 1997

(30) Foreign Application Priority Data

Jun. 5, 1996 (GB) .............................................. 9611698

(51) Int. Cl.[7] .............................. A61L 2/00; A61M 1/14; A61M 1/34; A61M 1/36; G01N 23/12
(52) U.S. Cl. .............................. 422/22; 422/20; 422/21; 422/24; 422/44; 422/46; 250/438; 250/455.11
(58) Field of Search ............................. 250/438, 20, 21, 250/22, 492.3, 44; 422/24, 453.11, 454.11, 455.11, 46; 210/748, 4, 5, 6; 604/20

(56) References Cited

U.S. PATENT DOCUMENTS 2,309,124 A   1/1943  Knott
3,926,556 A * 12/1975 Boucher ........................ 422/44
5,227,637 A *  7/1993 Harold et al. ................ 250/438
5,433,738 A *  7/1995 Stinson ........................ 422/24

FOREIGN PATENT DOCUMENTS

WO    WO 92/11060    *  7/1992

* cited by examiner

Primary Examiner—Terrence R. Till
Assistant Examiner—Imad Soubra
(74) Attorney, Agent, or Firm—Alston & Bird LLP

(57) ABSTRACT

A device suitable for use in the sterilization of a fluid such as a biological fluid or a fraction thereof, containing lymphocytes and/or micro-organisms, comprising a vessel having an inlet and an outlet and a passage which extends non-tortuously therebetween. A heat exchange device with a heat exchange surface is in substantially direct thermal contact with the interior of the passage. A temperature controller maintains the temperature of fluid in the passage below a temperature at which fluid components may form insoluble particles during irradiation. The passage has a wall which is substantially transparent to a lymphocyte and/or micro-organism inactivating radiation. The passage contains a static mixer device for thoroughly mixing the fluid so as to bring the whole of the fluid into an irradiation zone extending along and adjacent the passage walls and into contact with the heat exchange surface.

21 Claims, 1 Drawing Sheet

IRRADIATION DEVICE AND METHOD FOR FLUIDS ESPECIALLY FOR BODY FLUIDS

Figure 1:
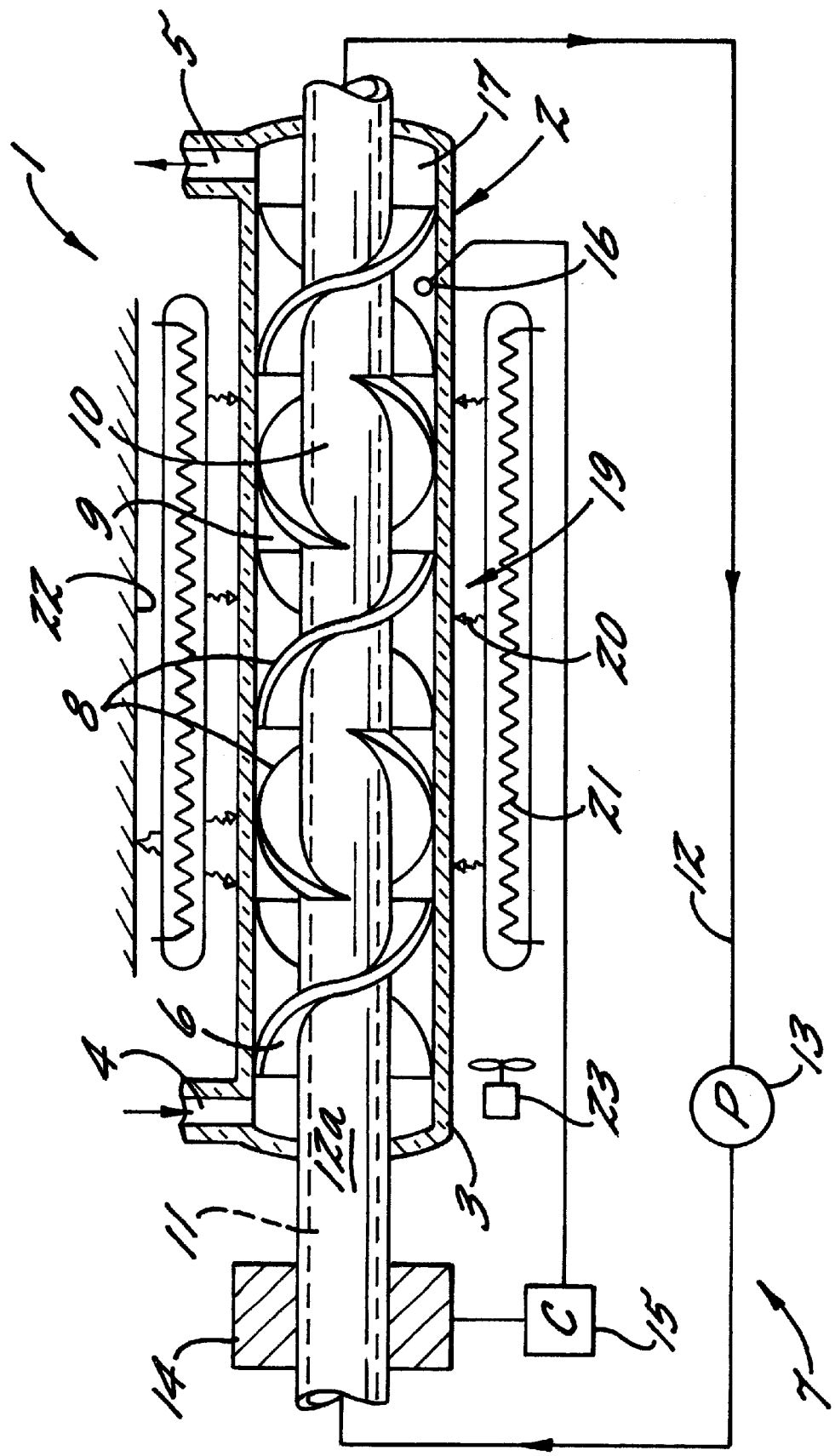

The present invention relates to the treatment of biological fluids, especially body fluids, and fractions thereof to inactivate selected components, e.g. lymphocytes, and microorganisms, including viruses and the like, in human blood and in particular to a device suitable for use in such a procedure.

Large amounts of body fluids such as blood and plasma and various fractions thereof are used in the treatment of patients suffering from a variety of conditions. Contamination of such fluids with various viruses and other microorganisms; however, can give rise to serious new conditions in the patients receiving these fluids and may even result in their death.

Although it has been known for some time that ultraviolet (UV) irradiation can inactivate lymphocytes and viruses, this was not a practical procedure because of the very low UV transmissibility of blood and hence the difficulty of ensuring a complete irradiation and inactivation. More recently we have considerably reduced this problem in our Patent No. GB 2200020 with the use of static mixers which provided a very thorough mixing of the fluid during irradiation thereby permitting a substantially even irradiation of the whole of the fluid.

We have now found, that fluids containing fibrinogen are susceptible to activation and formation of more or less large particles of polymeric fibrin. Such particles can moreover form around viruses and other microorganisms and thus screen them from the UV radiation thereby preventing inactivation thereof, and thus seriously risking the health of the recipient of the treated fluid. This fibrinogen activation can be readily triggered by mechanical stress e.g. shear forces present in mixing and by heat which can readily occur locally during irradiation. Insoluble particles of material can also be formed by thermal and/or mechanical denaturation of other proteinaceous components.

Such problems also arise with conventional sterilization of human blood products which generally involves incubation thereof at a temperature of the order of 78° C. for an extended period of time of perhaps 48 to 72 hours. This procedure further has the disadvantages of being relative time consuming and occupying substantial amounts of relatively large scale apparatus and may result in substantial loss of potency.

It is an object of the present invention to avoid or minimize one or more of the above disadvantages.

We have now found that by carefully controlling the temperature of the fluid and preventing any localized heating thereof, formation of particles which can screen viruses and other microorganisms from inactivating radiation, can be substantially prevented.

In one aspect the present invention provides a device suitable for use in use in the sterilization of a fluid, which is a biological fluid or a fraction thereof, containing lymphocytes and/or micro-organisms, which device comprises a vessel having an inlet and an outlet and a passage means extending substantially directly and non-tortuously therebetween, said passage means having a heat exchange device with a heat exchange surface in substantially direct thermal contact with the interior of the passage means, and a temperature control means formed and arranged for maintaining the temperature of fluid in the passage below a temperature at which fluid components may form insoluble particles during irradiation, and said passage means having wall means substantially transparent to a lymphocyte and/or microorganism inactivating radiation, said passage means containing a static mixer device formed and arranged for thoroughly mixing the fluid in use of the device, so as to bring substantially the whole of the fluid into an irradiation zone extending along and in substantially direct proximity to said wall means during passage between said inlet and said outlet and into contact with said heat exchange surface, whereby in use of the device substantially the whole of a body of said fluid passed through said vessel may be exposed to a similar substantial level of irradiation whilst maintaining it at a safe temperature.

Thus with a device of the present invention a particularly uniform treatment of the fluid with respect to both irradiation and temperature thereof may be achieved thereby avoiding on the one hand under-exposure to inactivating radiation whether as a result of screening by an excessive depth of soluble fluid components or by enveloping insoluble material formed by more or less direct thermal denaturation of fluid components or as a result of thermally and/or mechanically triggered reactions (such as fibrinogen activation), as well as avoiding localized overheating induced by the irradiation which can result in reduced inactivation and/or increased degradation, thereby on the one hand maximizing inactivation of lymphocytes (where required) and/or undesirable microorganisms and on the other hand minimizing denaturation and degradation of useful fluid components.

It will be appreciated that various forms of heat exchange device may be used including solid state devices such as Peltier effect devices. Conveniently though there is used a heat exchange device wherein is circulated a heat exchange fluid (e.g. gas, liquid, or liquid mixed with gas and/or frozen liquid) as this generally facilitates more precise control of the biological fluid temperature.

Conveniently there is used an annular form of vessel with an outer wall substantially transparent to lymphocyte and/or microorganism inactivating radiation and an inner wall constituting said heat exchange surface, the latter preferably being of a generally inert physiologically compatible material with high thermal conductivity e.g. stainless steel. Any suitable heat exchange fluid may be used e.g. water. Where a heat exchange fluid is used then the temperature of this may be controlled in various ways remotely from said heat exchange surface in the vessel e.g. using a solid state heat exchanger such as a Peltier-effect heat pump or a refrigeration coil etc.

Various forms of temperature control means may be used. In general there is used a variable rate cooling device provided with a controller for varying the cooling rate according to an input from a temperature sensor means disposed in thermal connection with at least one of the fluid passage means, the heat exchange surface, and a heat exchange fluid passage in said heat exchange device.

It will be appreciated that the "safe" temperature limits for avoiding denaturation and/or other thermally triggered reaction may vary from one biological fluid or fraction thereof to another, and also depending on the application of the fluid, and conveniently there is used a temperature control means which allows for the fluid temperature to be maintained at a plurality of different values as required. In general for any body fluids containing fibrinogen the temperature is desirably maintained at not more than 37° C., preferably from −5 to 37° C., advantageously from −5 to 19° C.

In a preferred aspect of the invention the device includes at least one microorganism inactivating radiation source mounted in more or less closely spaced proximity to said transparent wall means (for the avoidance of doubt it should be noted that references to the transparent wall means merely indicates substantial transmission of the inactivating radiation which may or may not be accompanied by significant transparency at other wavelengths e.g. visible light). The mounting of the radiation source is generally arranged to minimize undesired heating of the transparent wall means and biological fluid in contact therewith whilst maximizing the radiation intensity in the irradiation zone. Depending on the source used this generally positioned at from 1.5 to 5 mm from the transparent wall.

Various lymphocyte and/or microorganism inactivating radiations may be used, though UV is generally preferred, especially UV radiation having a wavelength range from 100 to 400 nm preferably from 200 to 350 nm, for example UVA at approximately 320 to 500 nm. UVB at approximately 310 nm and UVC at approximately 254 nm.

Suitable UV lamp sources are readily available commercially. Particular lamp sources which may be mentioned include those available from GTE Sylvania Ltd. of Charlestown, Shipley, West Yorkshire. Thorn EMI of Enfield, Middlesex and Philips Lighting of Croydon, Surrey, all in United Kingdom.

It should also be noted that the present invention also includes within its scope indirect inactivation of microorganism whereby a photoactivatable drug is incorporated in the fluid, said drug being converted from a non-activating form into a microorganism inactivating form by U.V. irradiation. One example of a photoactivatable drug of this type that may be mentioned is a psoralen e.g. 8—methoxy psoralen which upon exposure to U.V.—A radiation of 320 to 400 nm wavelength becomes capable of forming photo-adducts with DNA in lymphocytes thereby inactivating these.

Where UV radiation is used to effect inactivation then the vessel side wall means may be made of various UV—transparent materials including for example silica and other UV—transparent glasses such as those available under the Trade Names Spectrosil and Vitreosil; silicones; cellulose products such as Cellophane (Trade Name); and plastics materials such as polytetrafluoroethylene (PTFE), fluoroinatedethylenepropylene (FEP), and preferably low density polyethylene (LDPE) or polyvinyl chloride (PVC). Other activating radiations that may be used include microwave radiation used in conjunction with e.g. a glass or ceramic vessel wall; infra-red radiation used in conjunction with e.g. a quartz vessel wall; ultrasound radiation used in conjunction with e.g. a stainless steel vessel wall.

The duration of irradiation required will depend on various factors such as the intensity, disposition, and number of sources used, the transmission characteristics of the vessel side wall material, the vessel configuration and hence the mixing efficiency therein and the surface area of the thin layer of fluid adjacent the vessel side wall, the length of the passage means in the vessel and the flow-rate of the fluid being treated, and hence the residence time of the fluid in the irradiation zone, as well as the nature of the fluid itself. The required duration may however be readily determined by simple trial and error using suitable techniques known in the art for assessing inactivation of the relevant microorganisms and further details are provided hereinbelow. In general the residence time in the vessel will conveniently be in the range from 5 seconds to 30 minutes, preferably from 30 seconds to 10 minutes, e.g. 2 minutes, and the vessel side wall material and thickness and the radiation sources are chosen and arranged, to provide an effective inactivating dosage of U.V. radiation within such a period.

It will moreover be appreciated that the required irradiation time can be achieved in a number of different ways including one or more of the following: use of vessels with irradiation zones of different length, varying the flow rate of the fluid, using a plurality of devices in series, and recycling the fluid through the device(s) a number of times, though generally it is highly desirable that the inactivation treatment system is designed so that the required level or irradiation is achieved in a single pass, especially where the inactivation treatment system is incorporated in a production line for the manufacture of various products e.g. IgG, Factor VIII etc. etc.

Whilst it is a particular advantage of the present invention that denaturation of useful body fluid components is minimized, there can advantageously be included in the body fluid one or more protectants such as rutin, Ascorbic acid (ca 1 mM), or Quercetin (ca 0.2 mM), which reduce still further any possible denaturation or degradation of useful components.

It will also be understood that the degree of mixing required to achieve complete irradiation will depend on various factors such as the transmissibility of the fluid to the inactivating radiation and the total depth of fluid in the vessel from the wall through which radiation is received. In general the lower the transmissibility and the greater the fluid depth, the greater will be the number of mixer elements and mixing stages required.

Further preferred features and advantages of the invention will appear from the following detailed description given by way of examples and illustrated with reference to the accompanying drawings in which:

FIG. 1 is a partly schematic partly sectioned view of an irradiation apparatus of the present invention.

FIG. 1 shows an apparatus 1 comprising a vessel 2 in the form of a cylindrical tube 3 of quartz or other UV—transmissible material with an inlet 4 and an outlet 5, with an axially extending static mixer device 6 provided with temperature control means 7. In more detail the static mixer device 6 comprises an axially extending series of angularly offset helical "screw" elements 8 defining pairs of flow paths which are divided equally and mixed at the junctions 9 between successive elements 8 thereby providing a degree of mixing which increases exponentially with the number of elements used.

The "screw" elements 8 are mounted on a hollow core 10 which defines a heat exchange fluid passage 11 forming part of the temperature control means 7. In more detail the temperature control means 7 comprises a heat exchange fluid circuit 12 provided with pump means 13 for circulating the heat exchange fluid 12a therethrough and a Peltier-effect heat exchange device 14 provided with a control means 15 which has a temperature sensor 16 mounted inside the vessel 3 for monitoring the temperature of the fluid undergoing irradiation. The control means 15 is formed and arranged for controlling the rate of cooling supplied so as to maintain a desired fluid temperature. This may be a fixed value, or more conveniently the control means 15 may be provided with user operable input means for varying the desired temperature setting.

The core 10 (and desirably also the screw elements 8) are of an inert physiologically acceptable thermally conductive material such as stainless steel in order to facilitate efficient thermal transfer between the fluid being treated 17 and the heat exchange circuit 7 thereby to control the fluid temperature closely within relatively narrow limits so as to on the one hand maximize the efficiency of the sterilization/inactivation treatment and on the other hand to minimize any undesired denaturation or degradation of useful fluid components.

Irradiation 20 is effected by means of a plurality of UVC-emitting fluorescent tubes 21 extending parallel to and closely spaced from the vessel 3 and angularly distributed therearound. Advantageously reflectors 22 are provided to help concentrate the radiation 20 onto the vessel. The irradiation chamber may also be cooled by a fan 23. The vessel 3 is made of quartz in order to maximize transmission of the radiation 20 into the fluid 17 being treated and has diameter of approximately 20 mm, and a mixer 6 with a length of 300 mm and 10 elements.

The pump means 13 advantageously is provided with a flow rate controller in order to vary the flow rate of the fluid 12a to adjust the residence time of the fluid in the vessel 3 in the irradiation zone 19 and also to minimize denaturation or degradation of useful fluid components arising from mechanical stress in and around the static mixer 6. In general there may be used a flow rate of the order of 1 cm/sec to 100 cm/sec preferably 2 cm/sec to 50 cm/sec, desirably from 5 to 20 cm/sec.

It will be appreciated that the vessel 3 and mixer 6 may be found and arranged so that complete irradiation may be achieved with a single pass of the fluid through the vessel. Alternatively though a plurality of passes may be used to achieve full irradiation.

Use of the apparatus will be further explained in the following illustrative example.

EXAMPLE 1

Treatment of Human Plasma

Irradiation was carried out using an irradiation device having four 500 mm long UVC light sources distributed around 6 mm internal diameter PTFE tube containing a 34 cm long static mixer of the type shown in FIG. 1 with 48 screw elements. The fluid was circulated through the quartz tube, and a cooling device mounted in series therewith, at a flow rate of 100 ml/min which corresponded to an irradiation time of approximately 6.2 seconds for each passage. The fluid was circulated until a total effective irradiation time of approximately 100 seconds was achieved and the temperature thereof maintained at around 6.5° C.

Using plasma samples (200 ml) into which has been introduced a bacteriophage virus (2 ml) selected from: X174 and MS-2 (single-strand DNA and RNA respectively); T4 (double-strand DNA) and PR7772 (double strand DNA, enveloped), a virus kill in the region of 5–6 logs (i.e. over 99.999%) was achieved. At the same time the coagulation factor activity of key components of the plasma was substantially maintained as follows:

| Factor CIII:C | 57.3 ± 4.2% |
|---|---|
| Factor V | 38.8 ± 10.4% |
| Fibrinogen | 63.5 ± 4.2% |
| APTT | 18.5 ± 3.4% |

In a further experiment rutin (1.6 mM) was introduced into the plasma as a protectant and the retained coagulation factor activity was increased to over 85% whilst maintaining the virus inactivation level.

EXAMPLE 2

Using substantially similar procedures a human immunoglobulin preparation (150 g of IgG per litre) containing MS-2 (1.5 g) was subjected to an effective irradiation time of 300 seconds.

A virus inactivation level of 4.8 logs was achieved whilst aggregate formation increased from an initial level of 7.0% to only 7.6%.

Sterilization of the blood is monitored by one or more of the following procedures:
 (a) Separation of lymphocytes, culture and subsequent dosage with tritiated thymidine and subsequent liquid scintillation counting.
 (b) Separation of lymphocytes, culture and examination by electron microscope.
 (c) Separation of lymphocytes and observation of response to tissue stains.
 (d) Culture of bacteria by standard laboratory methods.
 (e) Growth of viruses by standard laboratory methods.
 (f) Study of Protozoans by light and electron microscopy and by in vivo passage in an animal species.
 (g) Study of biological behaviors of Blood Platelets by standard in vitro hematological techniques e.g. behavior in an agregometer and after exposure to collagen, ATP etc.

What is claimed is:

1. A device suitable for use in the sterilization of a fluid, which is a biological fluid or a fraction thereof, containing lymphocytes and/or micro-organisms, which device comprises a radiation source operable to produce a lymphocyte and/or micro-organism inactivating radiation, a vessel having an inlet and an outlet and a passage means extending substantially directly and non-tortuously therebetween, said passage means having a heat exchange device with a heat exchange surface extending along and in substantially direct thermal contact with the interior of the passage means, and a temperature control means formed and arranged for maintaining the temperature of fluid in the passage below a temperature at which fluid components may form insoluble particles during irradiation, and said passage means having wall means substantially transparent to said lymphocyte and/or micro-organism inactivating radiation, said passage means containing a static mixer device extending therealong and formed and arranged for thoroughly mixing the fluid in use of the device, so as to bring substantially the whole of the fluid into an irradiation zone extending along and in substantially direct proximity to said wall means during passage between said inlet and said outlet and into contact with said heat exchange surface, whereby in use of the device substantially the whole of a body of said fluid passed through said vessel may be exposed to a similar substantial level of irradiation whilst maintaining it at a safe temperature.

2. A device (1) as claimed in claim 1 wherein said heat exchange device (14) is a solid state Peltier-effect device.

3. A device (1) as claimed in claim 1 wherein said heat exchange device (14) comprises a conduit means (10) for the passage of a heat exchange fluid (12a) through the interior of said static mixer device (6) and in substantially direct thermal contact with an external surface of said static mixer device which constitutes said heat exchange surface of said heat exchange device.

4. A device (1) as claimed in claim 3 wherein said vessel (2) has an annular form with an outer wall substantially transparent to a lymphocyte and/or microorganism inactivating radiation (20) and an inner wall constituting said heat exchange surface (10).

5. A device (1) as claimed in claim 4 wherein the temperature of said heat exchange fluid (12a) is controlled (15) remotely from said heat exchange surface (10) in the vessel (2) by means of a solid state heat exchanger (14).

6. A device (1) as claimed in claim 4 wherein said temperature control means (7) is in the form of a variable rate cooling device provided with a controller (15) for varying the cooling rate according to an input from a temperature sensor means (16) disposed in thermal connection with at least one of said fluid passage means (3), said heat exchange surface (10), and the heat exchange fluid passage (11) in said heat exchange device (14).

7. A device (1) as claimed in claim 1 for use in the sterilization of a body fluid containing fibrinogen wherein said temperature control means is formed and arranged to maintain the temperature of said body fluid (17) at a temperature in the range of from −5° C. to +37° C.

8. A device (1) as claimed claim 1 which includes at least one lymphocyte and/or microorganism inactivating radiation source (21) mounted in more or less closely spaced proximity to said transparent wall means (3).

9. A device as claimed in claim 8 wherein said lymphocyte and/or microorganism inactivating radiation source is an ultra violet radiation source having an ultra violet radiation wavelength in the range of from 200 to 350 nm.

10. A device as claimed in claim 9 wherein said device is formed and arranged so as to be substantially free of any obstruction between said transparent wall means and said ultra violet radiation source.

11. A device (1) as claimed claim 1 wherein said side wall means (3) of said vessel (2) is made of substantially ultraviolet-transparent materials selected from the group including UV-transparent glasses, silicone, cellulose products, and plastics materials.

12. A device (1) as claimed in claim 1 wherein there may be used inactivating radiation and vessel wall material combinations selected from the group including microwave radiation used in conjunction with glass; infra-red radiation used in conjunction with a quartz vessel wall; or ultra sound radiation used in conjunction with a metal vessel wall.

13. A device (1) as claimed in claim 1 wherein there are provided reflectors (22) spaced around the vessel (2) formed and arranged to concentrate the radiation (20) onto said vessel.

14. A method of sterilizing a biological fluid (17) or fraction thereof, containing lymphocytes and/or microorganisms comprising the steps of:

providing a device (1) according to claim 1;

providing a lymphocyte and/or microorganism inactivating radiation source (21) in more or less closely spaced proximity to said transparent wall means of said device (1);

passing said fluid (17) through said passage means (3) of said device (1) so that the whole of a body of said fluid (17) is exposed to a similar substantial level of lymphocyte and/or microorganism inactivating irradiation; and operating said temperature control means (7) of said device (1) so as to maintain the temperature of the fluid (17) in the passage means (3) below a temperature at which fluid (17) components may form insoluble particles during irradiation.

15. A method as claimed in claim 14 which includes the step, prior to passing said fluid (17) through said passage means (3), of incorporating into the fluid (17) to be sterilized a photoactivatable drug, said drug being convertible from a non-activated form into a lymphocyte and/or microorganism-inactivating form by radiation (20).

16. A method as claimed in claim 14 which includes the step, prior to passing said fluid (17) through said passage means, of incorporating into the fluid (17) to be sterilized at least one protectant to reduce further any possible denaturation or degradation of useful fluid components.

17. A method as claimed in claim 14 wherein the residence time of fluid (17) in said vessel (2) of said device (1) is in the range of from 30 seconds to 10 minutes.

18. A device as claimed in claim 1 wherein said static mixer device comprises an axially extending series of angularly offset helical screw elements defining pairs of flow paths which are divided equally and mixed at junctions between successive elements.

19. A device as claimed in claim 18 wherein said screw elements are mounted on a hollow core which defines a heat exchange fluid passage.

20. A device as claimed in claim 19 wherein said core and screw elements are of an inert physiologically acceptable thermally conductive material.

21. A device as claimed in claim 20 wherein said thermally conductive material is stainless steel.

* * * * *

UNITED STATES PATENT AND TRADEMARK OFFICE
CERTIFICATE OF CORRECTION

PATENT NO.   : 6,464,936 B1
DATED        : October 15, 2002
INVENTOR(S)  : Mowat et al.

It is certified that error appears in the above-identified patent and that said Letters Patent is hereby corrected as shown below:

<u>Title page,</u>
Item [22], PCT Filed, "Aug. 18, 1997" should read -- May 29, 1997 --;
Item [86], PCT No., "PCT/DE97/01822" should read -- PCT/GB97/01454 --;
§371 (c)(1), (2), (4) Date, "Feb. 4, 1999" should read -- Dec. 4, 1998 --;
Item [56], References Cited, U.S. PATENT DOCUMENTS,
"Harold et al." should read -- Herold et al. --;
insert:
-- OTHER PUBLICATIONS
<u>Chemical Engineer's Handbook</u>, 4$^{th}$ Edition, Chapter II, pp.43-45, McGraw-Hill Book Company, New York --.

Signed and Sealed this

Eleventh Day of February, 2003

JAMES E. ROGAN
*Director of the United States Patent and Trademark Office*